(12) United States Patent
Mantovani et al.

(10) Patent No.: US 10,537,444 B2
(45) Date of Patent: Jan. 21, 2020

(54) SURGICAL AID FOR JOINTS

(71) Applicants: Matteo Mantovani, Carpi (IT); Fabio Catani, Budrio (IT)

(72) Inventors: Matteo Mantovani, Carpi (IT); Fabio Catani, Budrio (IT)

(73) Assignees: Matteo Mantovani, Carpi (IT); Fabio Catani, Budrio (IT)

( * ) Notice: Subject to any disclaimer, the term of this patent is extended or adjusted under 35 U.S.C. 154(b) by 225 days.

(21) Appl. No.: 15/549,915

(22) PCT Filed: Mar. 18, 2016

(86) PCT No.: PCT/IB2016/051534
§ 371 (c)(1),
(2) Date: Aug. 9, 2017

(87) PCT Pub. No.: WO2016/147153
PCT Pub. Date: Sep. 22, 2016

(65) Prior Publication Data
US 2018/0021151 A1    Jan. 25, 2018

(30) Foreign Application Priority Data
Mar. 19, 2015  (IT) .................. 102015902339316

(51) Int. Cl.
*A61F 2/46*    (2006.01)
*A61B 17/17*   (2006.01)
(Continued)

(52) U.S. Cl.
CPC .......... *A61F 2/4657* (2013.01); *A61B 17/025* (2013.01); *A61B 17/1764* (2013.01);
(Continued)

(58) Field of Classification Search
CPC ........................ A61F 2/4657; A61B 17/025
See application file for complete search history.

(56) References Cited

U.S. PATENT DOCUMENTS

2006/0241640 A1    10/2006  Briard et al.
2009/0326544 A1*   12/2009  Chessar ............... A61B 17/025
                                              606/102

(Continued)

*Primary Examiner* — Christian A Sevilla
(74) *Attorney, Agent, or Firm* — Pearne & Gordon LLP

(57) ABSTRACT

A surgical aid for joints which allows the positioning of mono-compartment or three-compartment prosthetic components so that the isometry of the capsular-ligament tissues of the knee is maintained during the entire range of motion. Such surgical aid comprises: a first element (10) intended to be positioned in contact with a first bone of a joint; a second element (20), intended to be positioned in contact with a second bone of the joint; the first and second element (10,20) being movable relatively to one another along at least a first direction (X); a displacement sensor (30) predisposed for measuring a relative displacement between the first and second element (10,20); an actuator/motor (50) predisposed for exerting a force that tends to move the first element (10) and second element (20) away from one another; a pressure sensor (40) which measures the force that is exerted between the first and second bone; a processing module (60) arranged to control the actuator/motor (50) so as to calculate the variation of the slope arising from the relationship between distance and force; the processing module (60) receives in input the signal emitted by the displacement sensor (30), the force sensor (10) and the pressure sensor (40).

12 Claims, 3 Drawing Sheets

(51) Int. Cl.
*A61B 17/02* (2006.01)
*A61B 90/00* (2016.01)
*A61B 17/00* (2006.01)

(52) U.S. Cl.
CPC ............... *A61B 2017/00398* (2013.01); *A61B 2017/0268* (2013.01); *A61B 2090/061* (2016.02); *A61B 2090/064* (2016.02)

(56) References Cited

U.S. PATENT DOCUMENTS

| | | | |
|---|---|---|---|
| 2010/0217156 A1* | 8/2010 | Fisher | A61F 2/38 600/587 |
| 2012/0172762 A1* | 7/2012 | Boyer | A61B 17/025 600/587 |
| 2012/0238911 A1 | 9/2012 | Chessar et al. | |
| 2014/0094715 A1 | 4/2014 | Stein et al. | |

* cited by examiner

SURGICAL AID FOR JOINTS

The invention relates to a surgical aid for joints.

The invention particularly relates to a surgical aid that helps to determine the orientation and extent of bone resections for implant of a mono-compartmental or three-compartmental prosthetic joint by keeping the periarticular or intra-articular capsule-ligamentous tissues in isometric tension during the entire range of motion. The device quantifies the distance between femur and tibia medially and/or laterally in the arthritic knee affected by mono- bi- or tri-compartmental osteoarthritis during the full range of motion, with the capsule-ligamentous structures being isometric and the extensor mechanism reduced.

The invention is particularly useful in the surgery intended for mono-bi-and-three-compartmental knee implants.

In brief, a total mono-compartmental, bi- or tri-compartmental prosthesis for the knee joint comprises a femoral element intended to be applied medially and/or laterally at the distal end of the femur, and a tibial element, intended to be applied medially and/or laterally to the proximal end of the tibia. When implementing the new knee joint, the osteo-cartilaginous ends of femur and tibia are replaced by the prosthetic femoral and tibial components.

The prosthetic tibial and femoral components are designed along geometrical criteria which promote stability and mobility of the new joint, without this causing any pain to the patient and enabling him/her to perform usual locomotor activities. The geometry of the prosthetic components and their three-dimensional alignment to the femur and the tibia have been recently defined via CT scan or MRI images in order that the anatomy of the knee joint is complied with.

To allow application of prosthetic femoral and tibial components, the corresponding femur and tibia ends must be resected so that the prosthesis becomes aligned with the mechanical or anatomical axis of the femur and tibia respectively.

Little attention has been paid till so far to the importance of maintaining the geometry and physiological stress of the capsule-ligament peri-articular or intra-articular tissues throughout the range of motion of the knee, with consequent optimization of articular biomechanics and particularly of stability, kinematics and proprioception of the knee and of the entire lower limb. Traditional surgical techniques as well as innovative techniques such as patient-oriented techniques, are geared towards changing the bone components anatomy (with alignment to the mechanical or anatomical axis), which implies in fact alteration of the soft tissue tension and change of the joint surfaces geometry. As a result, the kinematics and kinetics joint are completely altered as well as tension in the capsular ligamentous tissues. The femoral and tibial bone resections are made such as to ensure that the lower limb mechanical axis is passing through the center of the knee. The medial and lateral condylar bone resections are different in thickness due to the patients' anatomical variations and because they are aligned to the mechanical axis of the femur and tibia. Asymmetrical bone resections as well as modification of the geometry of articular surfaces of femur and polyethylene insert, inevitably result in an altered tension of the soft tissues, which soft tissues, when excessively tensioned, are often released surgically to their insertion or along the course.

In other words, the knee prosthesis implant surgery changes the anatomy of the femoral and tibial epiphysis in terms of alignment and surface geometry, regardless of the capsule-ligamentous tissues tensioning. All this can lead to unsatisfactory clinical results, accompanied by pain and difficulty on the part of the patient, not only in performing normal daily activities, but also in connection to locomotor activities desired by the patient.

Examples of devices which only in part solves the problems set out above are known from documents US2012172762 and US2012238911.

It is an object of the device herein disclosed to enable positioning of the prosthetic components by maintaining the capsule-ligamentous tissues in isometric conditions.

It is an aim of the present invention to further provide a surgical aid, which allows to position the prosthetic elements accurately, by maintaining the isometry of the peri-articular or intra-articular capsule-ligament structures according to the prosthetic design used.

An advantage of the surgical aid according to the present invention is to be compact and consequently little invasive, thus being positionable in a compartment or in both compartments with the extensor apparatus being reduced.

A further advantage of the surgical aid according to the present invention is that lengthening of the intervention time is not required.

Further characteristics and advantages of the present invention will better emerge from the detailed description that follows of a preferred embodiment of the invention, illustrated by way of non-limiting example in the accompanying figures in which.

With reference to the figures listed above, the surgical aid according to the present invention comprises a first element (10) intended to be positioned in contact with a first bone of a joint. In the case of a knee prosthesis, the first bone is the femur (F). In particular, the first element (10) is intended to be positioned in contact with the lower end of the femur. The surgical aid further comprises a second element (20) intended to be positioned in contact with a second bone of the joint. The second bone, in the case of knee implants, is the tibia (T). In particular, the second element (20) is intended to be positioned in contact with the tibia upper end, preferably following performance of a minimal tibial resection.

The first and second element (10,20) are movable relatively to one another along at least a first direction (X). An actuator or motor (50) is arranged to exert a force which tends to move away the first element (10) and the second element (20) from one another. Such actuator or motor (50) may be interposed between the first and second element (10,20). In the illustrated embodiment, the actuator or motor (50) is associated to one between the first and second element (10,20), for example, the second element (10), and is acting on the second element (20) with an active portion. The actuator or motor (50) comprises for example a hydraulic cylinder and/or a screw mechanism or other system in order to axially space apart the two elements from one another. In this case, the actuator body or motor (50) is associated to the second element (20), whereas the stem or spindle nut is associated to the first element (10).

Figure 1:
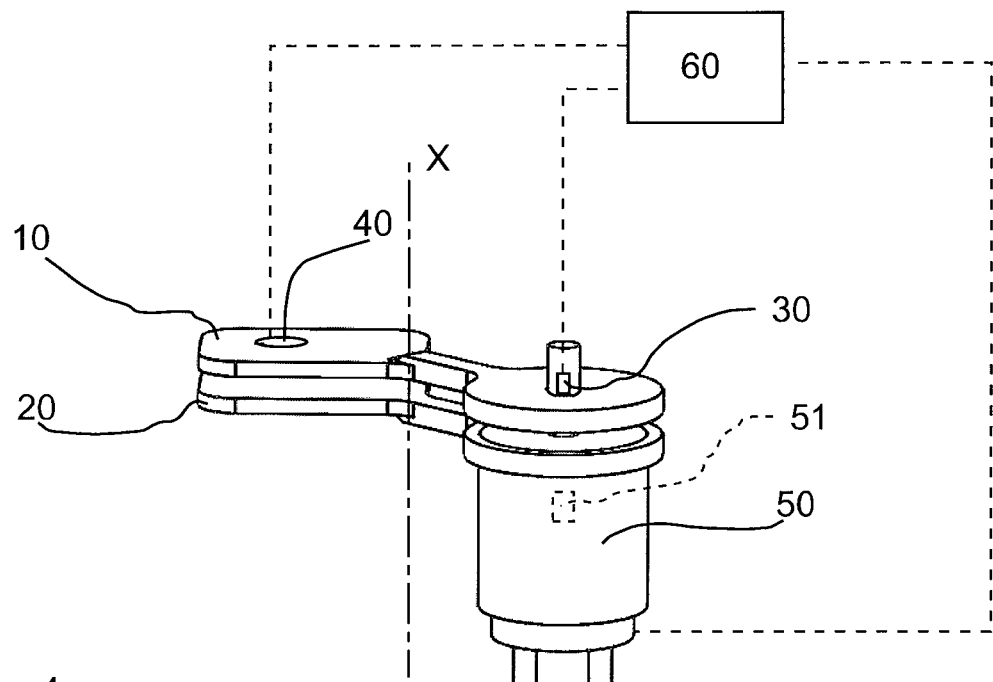
FIG. 1 shows a schematic view of the surgical aid according to the present invention.
Figure 2:
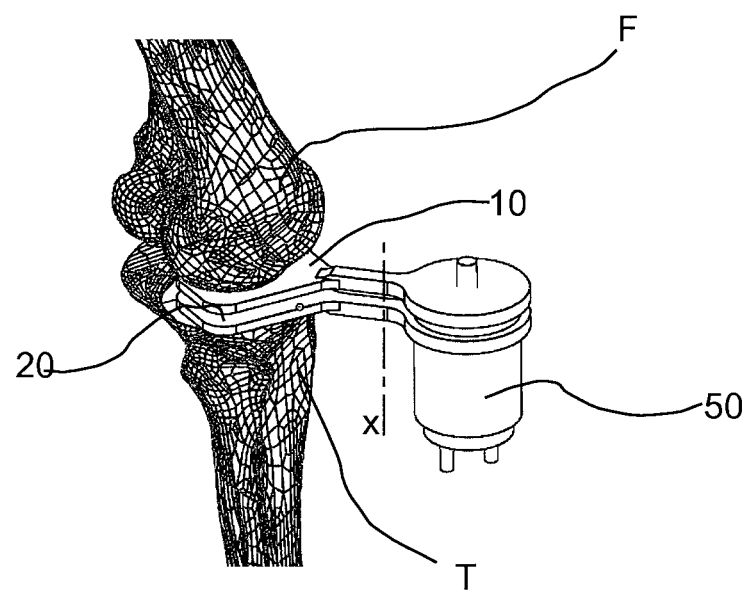
FIG. 2 shows a schematic view of the surgical aid of FIG. 1 in a configuration of use.
Figure 3:
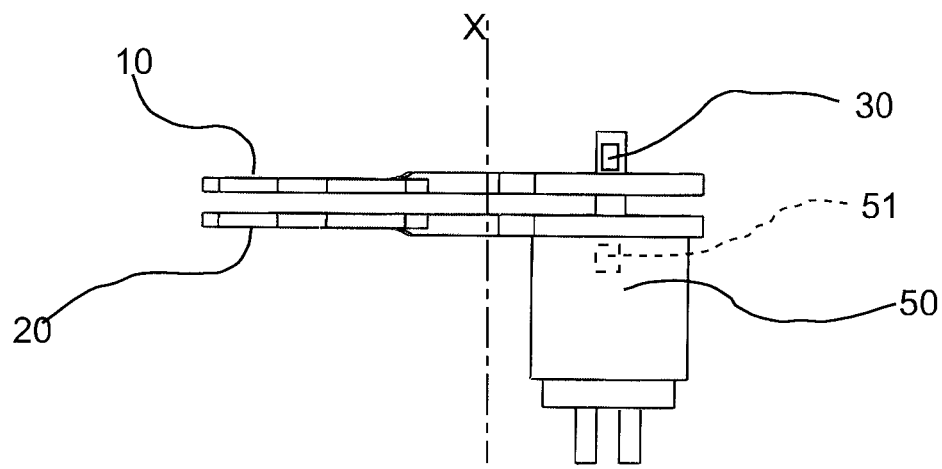
FIG. 3 shows the surgical aid of FIG. 1 in side view.

The surgical aid comprises a displacement sensor (30), which is predisposed for measuring a relative displacement between the first and second element (10,20). In particular, the displacement sensor (30) measures the relative displacement between the first and second element (10,20) with respect to zero or an initial pre-established position, wherein the first and second element (10,20) are located at a known distance. Essentially, this initial known distance is to be understood as the initial reference wherefrom the space between the tibia and femur is calculated during the entire range of motion. As shown in FIG. 1, the displacement sensor may be associated to the actuator or motor (50), such that displacement between the first and second element (10,20) may be detected by measuring the stroke performed by the actuator or motor (50). The surgical aid further comprises a force sensor (51), represented only schematically and predisposed for measuring the force exerted by the actuator or motor (50).

Preferably the surgical aid further comprises a pressure sensor (40), arranged for detecting a pressure which is acting on the first element (10) and/or second element (20). For example, the pressure sensor (40) may be associated with the first element (10) in an area intended to come into contact with the first bone (F) of the joint. The pressure sensor (40) can be useful for detecting the presence of any peaks of pressure or a possible uneven distribution of pressure, both indicating an incorrect positioning or conformation of the joint. This data is therefore desirable for ascertaining the positioning performed during the full range of motion.

The displacement sensor (30), the force sensor (51) and the pressure sensor (40), if present, are connected to a processing module (60), which is predisposed for controlling the actuator or motor (50). In particular the processing module (60) in different angular positions or joint flexion-extension all along the range of motion of the knee, progressively increases the force exerted by the actuator/motor (50) by simultaneously detecting the displacement measured by the displacement sensor (30) and developing a force-displacement diagram.

The isometric tension of the soft tissues is detected by the processing module (60) through an analysis of the force-elongation diagram obtained by reading the force sensor (51), the pressure sensor (40), if present, and the displacement sensor (30) in different angular or flexion-extension positions of the joint. In any pre-determined angular position, the distraction essentially ceases as soon as the force-displacement diagram exhibits a net slope change indicating the end of the isometric condition. For each angular or flexion-extension position selected for the joint, the processing module traces the force/displacement diagram as described above, thereby detecting the critical displacement value based on which the change in the slope of the force/displacement diagram occurs. Such critical displacement, for each selected angular position, substantially corresponds to the maximum distance between femur and tibia, wherein the capsule-ligamentous tissues are in isometric conditions. The number of angular positions or flexion-extension of the joint according to which the variation of the strength and development of the force/displacement diagram shall be performed, can be determined at will.

In each of the various selected angular positions, the processing module (60) then controls a variation of the force applied by the actuator/motor (50) up to the moment in which the variation of the slope of the force-displacement diagram is detected. At such time the processing module (60) detects the critical displacement between the first and second element (10,20). In this way, for each of the angular positions which were selected for the purposes of detection, the space or maximum tibiofemoral distance is obtained, in which the capsule-ligamentous tissues are in isometric conditions.

During the range of motion of the knee, in the different selected angular or flexion-extension positions, the processing module (60) is arranged to detect the displacement signal sent by the displacement sensor (30), which corresponds to the critical displacement along the first direction (X), i.e. to the displacement value based on which the change of slope of the force-displacement diagram occurs. The displacement values recorded for each angular position are stored and subsequently processed by means of a pre-determined algorithm, such that an optimal displacement can be obtained which corresponds essentially to a maximum tibiofemoral distance in which the capsule-ligamentous tissues are maintained in conditions of isometric tension, i.e. under conditions in which the capsule-ligamentous tissues are not subjected to a tension higher than that based on which the change of slope of the force-displacement curve is determined. This optimal displacement measured along the first direction (X), basically corresponds to the ideal height of the prosthesis, or at least of the tibial prosthetic component which exhibits a substantially flat articular surface.

Moreover, once the femoral and/or tibial resection have been performed based on the optimal displacement value between femur and tibia, which value is calculated by the module (60), one may use the surgical aid in order to verify the isometry of tissues throughout the range of motion of the limb. After entering the trial femoral component, the surface of which is compatible with the geometry of the permanent prosthesis, the surgical aid is inserted on the final resection of the tibia, and by moving the knee throughout the range of motion, the force/displacement measurements mentioned above are repeated, and the pressure measured by the sensor (40) possibly detected. Cutting, insert thickness or size of the components may still be modified as a function of the detected measurements for the purposes of trying to get the isometry of the medial and/or lateral capsular-ligamentous tissues throughout the whole range of motion. On the contact surface with the trial component of the femur, the surgical aid preferably exhibits a geometry which is equal to the final one of the tibial insert.

For the implant of a medial or lateral mono-compartmental prosthesis, the surgical aid according to the invention can be used as detailed hereinafter. The limb is suspended with a grip being exerted on the femur in order that the weight of the thigh does not affect the detection of the force between the femur and tibia.

Before the definitive resections of the femur and tibia are performed, the surgical aid is inserted between the ends of the articular bones, with the first and second element (10,20) being arranged in contact with the ends of the bones themselves. In order to make this possible, a preliminary resection of the tibia is preferably carried out, by following the mechanical or anatomical axis of the tibia on the frontal and sagittal planes. The femur is retained intact (without bone resection).

The joint is then brought from full extension to full flexion, for example within a range between 0° (straight leg) and 150°. In a certain pre-determined number of angular positions, the force applied by the actuator/motor (50) is varied and the first and second element (10,20) are moved with respect to one another, up to the point in which the force-displacement curve processed by the processing module (60) is changed from a non-linear trend to a linear trend, wherein the tension value of the isometric capsule-ligamentous tissues is indicated, as well as the corresponding critical displacement value which is stored by the module (60) itself. In each of the angular positions in which the measurement is carried out, the processing module (60) stores the isometric force value (or isometric tension) as well, at which value the trend of the force/displacement curve is changed from a non-linear trend to a linear trend.

Once detections have been completed, or after completion of the articular rotation between the bones, an optimal displacement value (or space) between the femur and tibia is determined by the processing module (60), according to the algorithm already mentioned. The optimal displacement calculated, essentially corresponds to the overall thickness of the prosthesis or at least the prosthetic tibial component, and allows performance of a correct spatial orientation of the same. This enables to obtain a joint kinematics of the prosthetic components which is compatible with the isometry of the capsule-ligament intra and extra articular structures.

Figure 4:
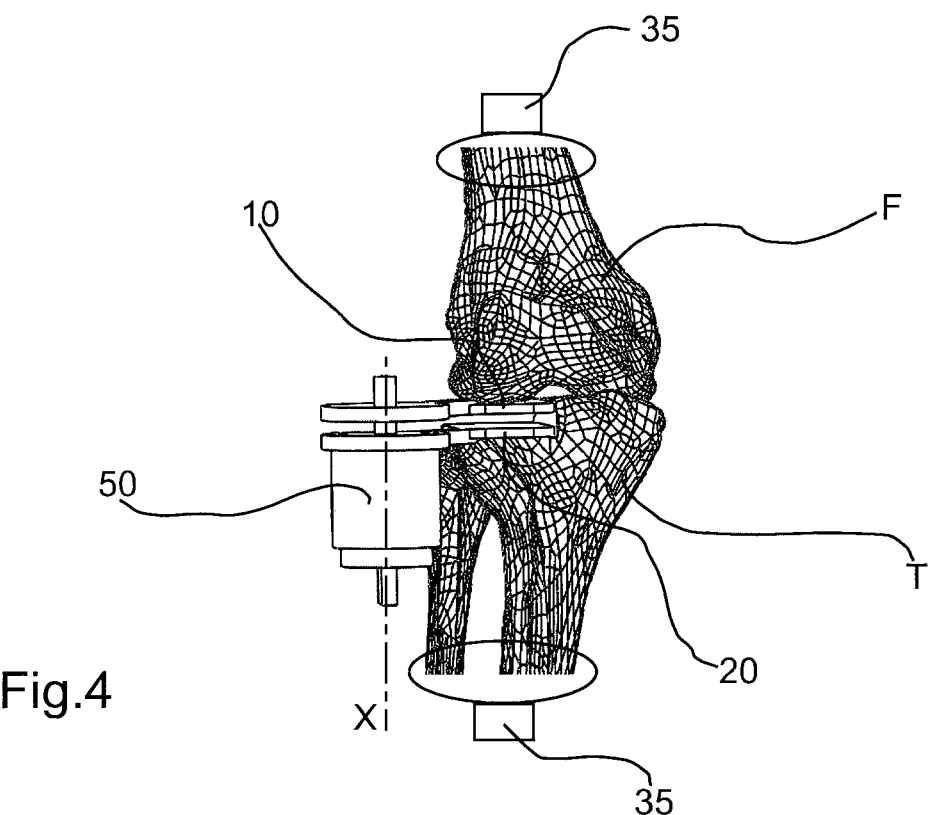
FIG. 4 shows the surgical aid of FIG. 3 in use configuration.
Figure 5:
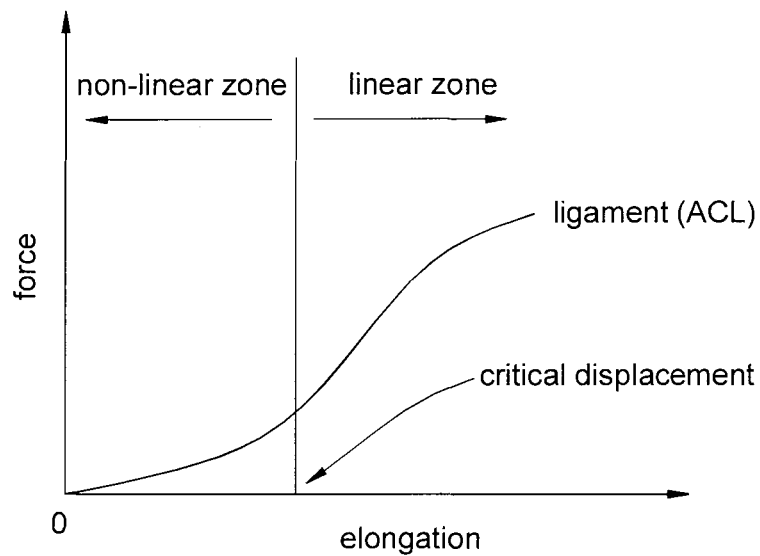
FIG. 5 shows an example of force/elongation curve for tendons and ligaments.

The surgical aid according to the present invention may be further provided with an angular measurement device (35), arranged to measure an angle of inclination between the two bones of the joint, which angular measurement device (35) is connected to the processing module (60). Such angular measurement device may be for example in the form of an inertial sensor. In a possible embodiment, the angular measurement device comprises a pair of inertial sensors (illustrated schematically in FIG. 4), arranged to be associated respectively to the femur and the tibia. For example, a first sensor can be associated to the thigh (by means of a band or the like), whereas a second sensor can be associated to the tibia or to the patient's ankle.

The processing module (60) is predisposed for detecting the signals emitted by the displacement sensor (30) and the angular measurement device (35) and for tracing a variation of the displacement along the first direction (X), in function of the angle of inclination between the two bones of the joint. In other words, the processing module (60) is arranged to draw an angle/displacement diagram.

The angular measuring device (35) may be used advantageously to approximate or to obtain an articular surface of the prosthesis, or at least the prosthetic tibial component.

In a first possible method of use, after determining the optimal displacement and the isometric tension value according to the previously described mode, it is possible to maintain the force exerted by the actuator or motor (50) to a value corresponding to said isometric tension. By making the articular bones to rotate between two pre-determined angular positions, a displacement between the first and second element (10,20) is produced, which is detected by the displacement sensor (30). At the same time, by means of the angle measurement device (35), the angular displacement between the articular bones is detected. The processing module (60) is able to correlate the displacement between the articular bones along the first direction (X) with the angle of inclination between the articular bones by drawing a curve which is able to define, rather well, the profile of the articular surface of the tibial prosthesis seen in projection on the sagittal plane. The correlation angle/displacement curve thus obtained and illustrated only qualitatively in FIG. 6, may be used to optimally select a ready-to-use prosthesis, or to shape ex novo a custom-made prosthesis.

Figure 6:
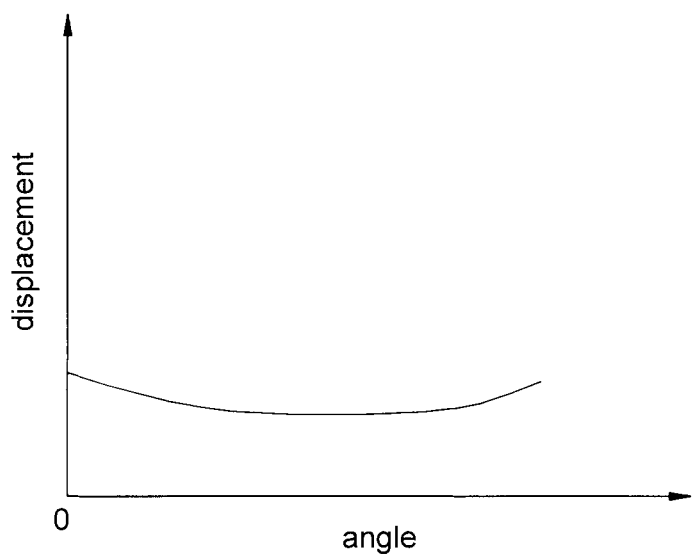
FIG. 6 shows a qualitative example of an angle/shifting curve obtained with the surgical aid according to the present invention.

In a second possible method of use, the angle of rotation between the articular bones is detected in any angular position based on which it is decided to perform the force-displacement measurement in the manner already described above. For example, starting from a substantially extended leg condition (angle close to 0°) and for a certain number of angular positions up to an angle of 150°, the processing module (60) detects the critical displacement as already described, and puts the latter in correlation with the corresponding angle detected via the sensor (35). In this way, to each angle a respective critical displacement is associated, which critical displacement, as already mentioned, corresponds to the displacement wherein the change of slope of the force-displacement curve occurs; in this manner an angle/displacement trend is delineated which is shown in FIG. 6, which approximates the profile of the articular surface of the tibial prosthesis seen in the sagittal plane.

In all the procedures herein disclosed, following resections and insertion of the trial femoral component, the surgical aid may be repositioned on the final resection of the tibia and the isometry of the capsule-ligamentous tissues in the medial or lateral compartment may be tested. This allows to make possible changes in bone resections, or to quantify and change the tension of the capsular ligamentous tissues.

In order that the orientation and extent definition of bone resections with respect to the femur and the tibia are accurate for the patient, relevant data shall be processed with a computer-assisted navigation and/or robotics system, wherein femur and tibia geometric images are obtainable via CT or NMR. The surgical aid may be further used by realizing cutting templates for the anatomical positioning of the femoral and tibial component via CT or NMR images, in order to optimize and possibly change the position of prosthetic components as a function of the optimal ligamentous tension.

The same technique may be applied in realizing monocompartmental prosthesis, bi-compartmental-Cruciate-Retaining full prosthesis, as well as posterior-Cruciate-Retaining or replacing posterior-Cruciate full prosthesis, by employing two devices: one medial device and one lateral device. The surgical aid according to the present invention offers important advantages. It allows sizing and accurate positioning of the prosthetic elements, while maintaining the isometry of the capsule-ligamentous tissues. In addition, the surgical aid according to the invention is compact and not invasive. A further important advantage is given by the fact that use of the surgical aid does not request to lengthen the intervention time, since it is enough to place the surgical aid between the ends of the articular bones and perform a complete joint movement for obtaining an optimal positioning and sizing of prosthetic components. The surgical aid may be further employed as an instrument for testing and adjusting orientation of the components and of bone thicknesses removed together with the trial components.

The invention claimed is:

1. A surgical aid for joints, comprising: a first element (10), intended to be positioned in contact with a first bone of a joint; a second element (20), intended to be positioned in contact with a second bone of the joint; the first and second element (10,20) are movable relative to one another along at least a first direction (X); a displacement sensor (30) predisposed for measuring a relative displacement between the first and second element (10, 20); an actuator or motor (50) predisposed for exerting a force that tends to move away the first element (10) and second element (20) from one another; a force sensor (51) suitable for detecting the force exerted by the actuator or motor (50); a processing module (60) which receives in input signals emitted by the displacement sensor (30) and pressure sensor (40) and which is predisposed for controlling the actuator or motor (50); wherein the processing module (60) is predisposed for detecting the signals of the displacement sensor (30) and signals of the force sensor (51) and for processing a force/displacement diagram, which puts into correspondence a force value applied by the actuator or motor (50), which force is obtained from a value detected by the force sensor (51), with a corresponding displacement value detected by the displacement sensor (30);

wherein the processing module (60) is arranged to store, in at least two bending positions, the force/displacement diagram by detecting a displacement wherein the diagram exhibits a change of slope;

characterized in that the processing module (60) is provided with an algorithm to process the displacement values recorded and stored for each angular position to obtain a displacement which corresponds to a maximum tibiofemoral distance in which capsule-ligamentous tissues are maintained in conditions of isometric tension.

2. A surgical aid according to claim 1, wherein the processing module (60) is arranged to detect on the force/displacement diagram in at least two bending positions, the displacement in which the diagram is changing from a non-linear to a substantially linear trend.

3. A surgical aid according to claim 1, wherein the processing module (60) is arranged to detect the signals emitted by the displacement sensor (30) and force sensor (51) and, based on the detected signals, to process said force/displacement diagram in pre-determined angular positions between the bones of the joint.

4. A surgical aid according to claim 3, wherein the processing module (60) comprises an algorithm for processing points of the force/displacement diagrams in pre-determined angular positions in order that an optimal displacement is obtained, which is measured along the first direction (X) corresponding to the height of at least one prosthetic component.

5. A surgical aid according to claim 1, wherein the pressure sensor (40) is predisposed for detecting a pressure acting on the first element (10) and/or on the second element (20).

6. A surgical aid according to claim 1, comprising an angular measurement device arranged to measure an angle of inclination between the two bones of the joint, which angle of inclination is connected to the processing module (60).

7. A surgical aid according to claim 6, wherein the processing module (60) is arranged to detect the signals of the displacement sensor (30) and the angular measurement device and to trace a variation of the displacement along the first direction (X) as a function of the angle of inclination between the two bones of the joint.

8. A method for determining the resection of a first and/or second bone for implantation of a joint prosthesis, comprising the following steps:

inserting the surgical aid according to claim 1 between the first and second bone, so that a joint end of the first bone is in contact with the first element (10) and a joint end of the second bone is in contact with the second element (20);

varying the force exerted by the actuator/motor (50) in each of various pre-determined angular positions of the joint, and detecting the displacement measured by the displacement sensor (30) by developing a force-displacement diagram which puts in correspondence a value of force applied by the actuator/motor (50) with a corresponding displacement value detected by the displacement sensor (30);

in each of said various pre-determined angular positions of the joint, detecting and storing the displacement values measured by the displacement sensor (30) and force sensor, wherein the force-displacement diagram is changing from a non-linear to a substantially linear trend, or wherein a first change of slope in the force/displacement curve occurs;

processing the displacement values stored according to a pre-determined algorithm, in order that an optimal displacement is obtained, which is measured along the first direction (X), at which value an isometric tension of capsule-ligament structures is produced, namely a tension which substantially does not exceed the tension value corresponding to the changing of the force-elongation curve slope, wherein said determined displacement corresponds to the height of at least one prosthetic component.

9. A method according to claim 8, wherein, after that said optimal displacement and isometric tension have been determined, the following steps are provided:

maintaining the force exerted by the actuator or motor (50) at a value corresponding to said isometric tension of the capsule-ligament structures;

rotating the articular bones between two pre-determined angular positions;

tracing a variation of the displacement along the first direction (X), as a function of an angle of inclination between the two bones of the joint.

10. A method for implantation of a joint prosthesis, comprising the following steps:

determining the resection of the first and/or second bone by means of the method according to claim 8;

performing resection of the first and/or second bone;

implanting the prosthetic joint.

11. A method according to claim 9, comprising the following steps:

selecting or realizing at least one prosthetic component exhibiting a joint surface structured according to said displacement variation along the first direction (X) as a function of the angle of inclination between the two bones of the joint;

implanting the prosthetic component.

12. A method according to claim 10, wherein, after implantation of the prosthetic joint, the following steps are provided:

re-inserting the surgical aid between the first and second bone, so that the prosthesis portion associated with the first bone is in contact with the first element (10) and the prosthesis portion associated with the second bone is in contact with the second element (20);

performing the following steps:

inserting the surgical aid between the first and second bone, so that the joint end of the first bone is in contact with the first element (10) and the joint end of the second bone is in contact with the second element (20);

varying the force exerted by the actuator/motor (50) in each of the various pre-determined angular positions of the joint, and detecting the displacement measured by the displacement sensor (30) by developing a force-displacement diagram which puts in correspondence a value of force applied by the actuator/motor (50) with a corresponding displacement value detected by the displacement sensor (30);

in each of said various pre-determined angular positions of the joint, detecting and storing the displacement values measured by the displacement sensor (30) and force sensor, wherein the force-displacement diagram is changing from a non-linear to a substantially linear trend, or wherein a first change of slope in the force/displacement curve occurs;

processing the displacement values stored according to a pre-determined algorithm, in order that an optimal displacement is obtained, which is measured along the first direction (X), at which value an isometric tension of the capsule-ligament structures is produced, namely a tension which substantially does not exceed the tension value corresponding to the changing of the force-elongation curve slope, wherein said determined displacement corresponds to the height of at least one prosthetic component, thereby obtaining a new set of points which approximate a resection;

removing the prosthesis and performing a new resection of the first and/or second bone in accordance with the new set of points that approximate a resection, if the new set of points deviates from the previous set of points beyond a pre-set threshold.

* * * * *